United States Patent
Gao et al.

(10) Patent No.: US 12,365,763 B2
(45) Date of Patent: Jul. 22, 2025

(54) PHTHALONITRILE RESINS, METHODS OF MAKING SAME AND COMPOSITIONS THEREOF

(71) Applicant: Huntsman Advanced Materials Americas LLC, The Woodlands, TX (US)

(72) Inventors: Kuanqiang Gao, The Woodlands, TX (US); Naraso Borjigin, The Woodlands, TX (US); Tao Tao, The Woodlands, TX (US)

(73) Assignee: HUNTSMAN ADVANCED MATERIALS Americas LLC

( * ) Notice: Subject to any disclaimer, the term of this patent is extended or adjusted under 35 U.S.C. 154(b) by 528 days.

(21) Appl. No.: 17/772,276

(22) PCT Filed: Oct. 30, 2020

(86) PCT No.: PCT/US2020/058099
§ 371 (c)(1),
(2) Date: Apr. 27, 2022

(87) PCT Pub. No.: WO2021/087193
PCT Pub. Date: May 6, 2021

(65) Prior Publication Data
US 2023/0023657 A1    Jan. 26, 2023

Related U.S. Application Data

(60) Provisional application No. 62/928,466, filed on Oct. 31, 2019.

(51) Int. Cl.
| | | |
|---|---|---|
| C08G 73/06 | (2006.01) | |
| C07D 307/42 | (2006.01) | |
| C08G 8/06 | (2006.01) | |
| C08G 8/36 | (2006.01) | |
| C08G 73/02 | (2006.01) | |
| C08G 73/22 | (2006.01) | |
| C08J 5/04 | (2006.01) | |
| C08J 5/24 | (2006.01) | |

(52) U.S. Cl.
CPC ....... *C08G 73/0672* (2013.01); *C07D 307/42* (2013.01); *C08G 8/06* (2013.01); *C08G 8/36* (2013.01); *C08G 73/0233* (2013.01); *C08G 73/024* (2013.01); *C08G 73/065* (2013.01); *C08G 73/22* (2013.01); *C08J 5/04* (2013.01); *C08J 5/249* (2021.05); *C08J 2379/04* (2013.01)

(58) Field of Classification Search
CPC .. C08G 8/06; C08G 8/36; C08G 73/06–0661; C08G 73/0672; C08G 73/024; C08G 8/04; C07C 255/51; C07C 255/54
See application file for complete search history.

(56) References Cited

U.S. PATENT DOCUMENTS

| | | |
|---|---|---|
| 4,650,838 A | 3/1987 | Das et al. |
| 7,786,219 B2 | 8/2010 | Ishii et al. |
| 8,222,403 B2 | 7/2012 | Laskoski et al. |
| 2009/0215943 A1 | 8/2009 | Hirose et al. |
| 2014/0275472 A1 | 9/2014 | Keller et al. |

FOREIGN PATENT DOCUMENTS

| | | | |
|---|---|---|---|
| CN | 104086727 A | 10/2014 | |
| CN | 107915819 A | 4/2018 | |
| RU | 2580927 C1 | 4/2016 | |
| RU | 2014135227 A | 5/2016 | |
| RU | 2018106457 A | 8/2019 | |
| WO | 99/18092 A1 | 4/1999 | |
| WO | 2008/0028970 A2 | 1/2008 | |
| WO | 2012/015604 A1 | 2/2012 | |
| WO | WO-2017105890 A1 * | 6/2017 | ............. C08G 14/06 |

OTHER PUBLICATIONS

Yang et al. "Design a Phthalonitrile/Benzoxazine Blend for Advanced GFRP Composite Materials", Chinese J Polym. Sci 2018, vol. 36(1), pp. 106-112, abstract; p. 104 col. 1 para 4-col. 2 para 3; Scheme 1; p. 111, col. 2, para 2.
International Search report and Written Opinion mailed Feb. 2, 2021 issued in corresponding application No. PCT/US2020/58099.
Kim H J et al. "Synthesis and thermal characterization of polybenzoxazines based on acetylene-functional monomers", Polymer, Elsevier, Amsterdam, NL, vol. 40, No. 23, Jul. 10, 2001 (Jul. 10, 2001), pp. 6565-6573, XP004177288. ISSN: 0032-3861, DOI: 10.1016/S0032-3861 (99) 00046-4, *title; abstract * p. 6570-p. 6571; tables 1, 2*.
European Search report and Written Opinion mailed Oct. 17, 2023 issued in corresponding application No. 20881476.4.
International Search report and Written Opinion mailed Jan. 26, 2021 issued in corresponding application No. PCT/US2020/58107.
Office Action received in corresponding Russian Application No. 2022114447 issued Mar. 28, 2024.

\* cited by examiner

*Primary Examiner* — Kregg T Brooks
(74) *Attorney, Agent, or Firm* — HUNTSMAN ADVANCE; David K. Wooten (57) ABSTRACT

The present disclosure provides a functionalized phthalonitrile monomer derived from a polyhydric phenol comprising at least one furan group or thiophene group and 4-nitrophthalonitrile. The functionalized phthalonitrile monomer may be used in various thermosetting compositions which can be cured to form thermoset polymers having excellent thermal and mechanical properties, such as high thermal stability, heat resistance, high char yield, and enhanced structural rigidity.

1 Claim, 7 Drawing Sheets

PHTHALONITRILE RESINS, METHODS OF MAKING SAME AND COMPOSITIONS THEREOF

CROSS-REFERENCE TO RELATED APPLICATION

This application is the National Phase of International Application PCT/US2020/058099 filed Oct. 30, 2020 which designated the U.S. and which claims priority to U.S. Provisional Patent Application Ser. No. 62/928,466, filed Oct. 31, 2019. The noted applications are incorporated herein by reference.

STATEMENT REGARDING FEDERALLY SPONSORED RESEARCH OR DEVELOPMENT

Not applicable.

FIELD

The present disclosure generally relates to novel phthalonitrile resins, methods of making such phthalonitrile resins and their use in polymerizable thermosetting compositions for application in various industries, such as, but not limited to, the building and construction, electronics packaging, energy and power generation, aerospace, transportation and medical device industries.

BACKGROUND

Phthalonitrile monomers are a new class of high performance monomers developed for high temperature applications, such as in the production of prepregs, laminates and structural composite parts. For example, U.S. Pat. Nos. 6,420,464, 8,039,576, 8,853,343, 9,920,165 and US Pat. Publ. No. 2019/0047946 disclose various phthalonitrile monomers derived from phenols, aromatic diols reacted with diphenyl acetylenes, polyphenols from renewable sources, and bisphenols. These phthalonitrile monomers, after curing, have been found to possess excellent thermal and thermo-oxidative stability with initial decomposition temperatures greater than 450° C., as well as a myriad of other highly attractive performance properties, such as enhanced flame-resistance, the absence of a glass transition temperature before thermal decomposition, good mechanical properties at high temperatures, low water uptake, excellent corrosion resistance and advanced UV-shielding behavior.

However, state of the art phthalonitrile monomers are known to suffer from brittleness due to the rigidity of the monomeric precursors and the high degree of cross-linking in the final cured product. Additionally, these phthalonitrile monomers are generally solid at room temperature and therefore must be melted prior to use. Moreover, they can require higher than desired curing temperatures (for e.g. above 250° C.) and longer times to fully cure.

To overcome these drawbacks, attempts have been made to adjust the chain length of the moieties between the phthalonitrile monomer units in order to reduce their melting point and improve the flexibility of the cured product. Different types of catalysts have also been used to improve the curing behavior of these phthalonitrile monomers. Finally, in order to improve the processability, curing behavior and final properties of the cured phthalonitrile product, U.S. Pat. No. 5,939,508 and WO 2017105890 disclose particular phthalonitrile monomers copolymerized with an epoxy or benzoxazine resin.

It would be desirable to further improve upon these state of the art phthalonitrile monomers by developing new phthalonitrile monomers which can be used in polymerizable thermosetting compositions that exhibit even better processability and curing behavior and produce cured products having improved thermal and mechanical properties.

SUMMARY

The present disclosure generally provides a functionalized phthalonitrile monomer obtained from the reaction of (i) a polyhydric phenol compound comprising at least one furan group or thiophene group and (ii) 4-nitrophthalonitrile.

According to another embodiment, there is provided a thermosetting composition including the functionalized phthalonitrile monomer and curing agent. In still another embodiment, the thermosetting composition may further include a second thermoset resin comprising at least one of a vinyl, ethynyl, maleimide, imino, cyano, oxazine or epoxy group, wherein the functionalized phthalonitrile monomer is the "first" thermoset resin.

The thermosetting compositions of the present disclosure may be cured to form thermoset polymers having improved thermal and mechanical properties. Accordingly, the thermosetting compositions can find use in a variety of applications, such as, but not limited to, the building and construction, electronics packaging, military, energy and power generation, aerospace, transportation and medical device industries.

DETAILED DESCRIPTION

The present disclosure generally provides a functionalized phthalonitrile monomer obtained from the reaction of (i) a polyhydric phenol compound comprising at least one furan group or thiophene group and (ii) 4-nitrophthalonitrile. It has been surprisingly found that the functionalized phthalonitrile monomers of the present disclosure offer several advantages over state of the art phthalonitrile monomers. For instance, the functionalized phthalonitrile monomers of the present disclosure contain furan/thiophene groups which are capable of homopolymerizing and cross-linking when cured to form thermoset polymerized products having improved thermal and mechanical properties, such as an increase in thermal stability, heat resistance, char yield, and enhanced structural rigidity. Additionally, the functionalized phthalonitrile monomers of the present disclosure are capable of reacting with other unsaturated thermoset resins to further improve processability, curing behavior and final cured product properties. Accordingly, the functionalized-phthalonitrile monomers of the present disclosure exhibit an excellent balance of physical, mechanical and thermal properties in the uncured and cured state as compared to those for state of the art phthalonitrile monomers.

The following terms shall have the following meanings:

The term "comprising" and derivatives thereof are not intended to exclude the presence of any additional component, step or procedure, whether or not the same is disclosed herein. In order to avoid any doubt, all compositions claimed herein through use of the term "comprising" may include any additional additive or compound, unless stated to the contrary. In contrast, the term, "consisting essentially of" if appearing herein, excludes from the scope of any succeeding recitation any other component, step or procedure, excepting those that are not essential to operability and the term "consisting of", if used, excludes any component, step or procedure not specifically delineated or listed. The term "or", unless stated otherwise, refers to the listed members individually as well as in any combination.

The articles "a" and "an" are used herein to refer to one or more than one (i.e. to at least one) of the grammatical object of the article. By way of example, "a functionalized phthalonitrile monomer" means one functionalized phthalonitrile monomer or more than one functionalized phthalonitrile monomer.

The phrases "in one aspect", "according to one aspect" and the like generally mean the particular feature, structure, or characteristic following the phrase is included in at least one aspect of the present disclosure, and may be included in more than one aspect of the present disclosure. Importantly, such phases do not necessarily refer to the same aspect.

If the specification states a component or feature "may", "can", "could", or "might" be included or have a characteristic, that particular component or feature is not required to be included or have the characteristic.

According to one aspect, the present disclosure provides a functionalized phthalonitrile monomer obtained from the reaction of (i) a polyhydric phenol compound comprising at least one furan group or thiophene group and (ii) 4-nitrophthalonitrile.

The polyhydric phenol compound comprising at least one furan group or thiophene group include those compounds derived from a phenol compound and a compound of the formula (1)

where X is oxygen or sulfur, Q is hydrogen or a $C_1$-$C_5$ alkyl group and j is an integer of 1 to 3. Such compounds of formula (1) include, but are not limited to, furfural, 3-furaldehyde, 3-methylfurfural, 5-methylfurfural, 5-ethylfurfural, 2-thiophene-carboxyaldehyde, 3-thiophene-carboxyaldehyde, 3-methyl-2-thiophene-carboxyaldehyde and the like.

The phenol compound can include, but is not limited to, phenol, cresol, xylenol (dimethylphenol) such as 2,6-xylenol, trimethylphenol, 2,5-alkylphenol, such as 2-tert-butyl-5-methyl-phenol or 2-tert-butyl-4-methylphenol, allylphenol, alkynyl phenol, octylphenol, phenylphenol, diphenylphenol, guaiacol, hydroquinone, resorcinol, catechol, naphthol, dihydroxynaphthalene, methyl naphthol, bisphenol A, bisphenol F and the like.

The above compounds of formula (1) and phenol compounds are not limited to those specifically cited above. Furthermore each of the compounds of formula (1) and phenol compound may be used alone or as a mixture of two or more.

The polyhydric phenol compound comprising at least one furan group or thiophene group may be prepared by methods generally known to those skilled in the art. For example, the phenol compound may be condensed with the compound of formula (1) in the presence of a base and optionally an alcohol or mono-substituted benzene at a temperature of between about 30° C. to about 150° C., or between about 60° C. to about 90° C. In general, the amount of the phenol compound and the compound of formula (1) present during condensation may range from between about 1.5 moles to about 20 moles of the phenol compound per 1 mole of the compound of formula (1). In some embodiments, the amount of the phenol compound to the compound of formula (1) present during condensation may range from between about 1.8 moles to about 10 moles of the phenol compound per 1 mole of the compound of formula (1).

Examples of bases which can be used include, but are not limited to, alkaline metal hydroxides, such as lithium hydroxide, sodium hydroxide, potassium hydroxide, etc.; alkaline earth metal hydroxides, such as magnesium hydroxide, calcium hydroxide, etc.; alkaline metal alkoxides, such as sodium methoxide, sodium ethoxide, potassium methoxide, potassium ethoxide, potassium-tert-butoxide, etc.; and alkaline earth metal alkoxides, such as magnesium methoxide, magnesium ethoxide, etc. These bases can be used alone or in combination of two or more. The base may be used in an amount of between about 0.005 moles to about 2.0 moles per 1 mole of the phenol compound, or between about 0.01 to about 1.1 moles per 1 mole of the phenol compound.

The alcohol or mono-substituted benzene solvents which may be used include, but are not limited to, methanol, ethanol, propanol, isopropanol, toluene, xylene and the like, which can be used alone or as a mixture. When required, such solvents may be used in an amount of between about 5 parts by weight to about 500 parts by weight per 100 parts by weight of the phenol compound, or between about 10 parts by weight to about 300 parts by weight per 100 parts by weight of the phenol compound.

The reaction may be carried out by adding the base to a mixture of the phenol compound and the compound of the formula (1) (and optionally alcohol or mono-substituted benzene solvent) and heating the resulting mixture. Alternatively, the compound of formula (1) may be added to a mixture of the phenol compound and the base (and optionally alcohol or mono-substituted benzene solvent) under heating. The reaction time may range from between about 5 hours to about 100 hours. After the reaction has run to completion, the reaction mixture may be neutralized. Any unreacted materials may be subsequently removed by filtration or by heating in vacuum.

According to one embodiment, the polyhydric phenol compound comprising at least one furan group or thiophene group is a compound selected from the formulas (2) to (10)

where n is an integer from about 3 to about 3.2.

In still another embodiment, the polyhydric phenol compound comprising at least one furan group or thiophene group is derived from bisphenol A or bisphenol F and the compound of formula (1) where X is oxygen and Q and j are defined as above.

The polyhydric phenol compound comprising at least one furan group or thiophene group is then reacted with 4-nitrophthalonitrile to form the functionalized phthalonitrile monomer of the present disclosure.

According to one embodiment, the polyhydric phenol compound comprising at least one furan group or thiophene group is reacted with 4-nitrophthalonitrile in the presence of a catalyst and optionally a solvent. Examples of catalysts include, but are not limited to, the bases described above, as well as alkali metal salts, such as cesium carbonate, potassium carbonate or sodium carbonate, organolithium reagents, such as methyl or n-butyl lithium, Grignard agents, or any combination thereof. Examples of solvents which may be used include, but are not limited to, any polar or nonpolar solvent such as acetone, acetonitrile, an alcohol, methylethylketone, methylisobutylketone, dimethylformamide, n-methylpyrrolidone, dimethylsulfoxide, hexamethylphosphoramide or combinations thereof. In another embodiment, the solvent may be a solvent capable of forming an azeotrope with water, such as toluene or xylene. It has been surprisingly found that such solvents may be used to assist in the removal of both the water found in the compounds which form the reaction mixture (i.e. the polyhydric phenol compound comprising at least one furan or thiophene group, 4-nitrophthalonitrile and base) as well as the water formed during the reaction of the polyhydric phenol compound comprising at least one furan group or thiophene group and 4-nitrophthalonitrile. The functionalized phthalonitrile may be purified by recrystallization from a mixture of solvent and water to enrich the monomer content of the resulting product.

According to another embodiment, the polyhydric phenol compound comprising at least one furan group or thiophene group and functionalized phthalonitrile monomer may be formed in the same reaction vessel to improve overall process time and efficiency. In such embodiments, in a first step, the polyhydric phenol comprising at least one furan group or thiophene group is formed in a reaction vessel as described above. In a second step, 4-nitrophthalonitrile is added to the polyhydric phenol comprising at least one furan group or thiophene group in the reaction vessel to form the functionalized phthalonitrile monomer. The base, catalyst and solvents which are used in the reactions in the first step and second step may be the same or different. In some embodiments, the solvent is toluene or xylene.

The functionalized phthalonitrile monomer of the present disclosure may be cured by heat to form a thermoset polymer exhibiting an excellent balance of chemical, mechanical and thermal properties. A curing agent may be used to speed up thermoset formation. Thus, according to another embodiment, there is provided a thermosetting composition comprising the functionalized phthalonitrile monomer and a curing agent.

The amount of the functionalized phthalonitrile monomer present in the thermosetting composition may be in an amount of at least about 1% by weight, at least about 5% by weight, or at least about 10% by weight, or at least about 20% by weight, or at least about 30% by weight, or at least about 40% by weight, or at least about 50% by weight, or at least about 60% by weight, or at least about 70% by weight, or at least about 80% by weight, or at least about 90% by weight, or at least about 99% by weight, based on the total weight of the thermosetting composition. In other embodiments, the amount of functionalized phthalonitrile monomer present in the thermosetting composition may be in an amount of between about 1% by weight to about 99% by weight, or between about 5% by weight to about 90% by weight, or between about 10% by weight to about 80% by weight, or between about 20% by weight to about 70% by weight, or between about 30% by weight to about 60% by weight, based on the total weight of the thermosetting composition.

The curing agent which may be used includes, but is not limited to, aromatic amines, primary amines, secondary amines, diamines, polyamines, amine-substituted phosphazenes, phenols, strong acids, organic acids, strong organic acids, inorganic acids, metals, metallic salts, metallic salt hydrates, metallic compounds, halogen-containing aromatic amines, clays, and chemically modified clays. The use of clays or chemically modified clays may improve the mechanical and flammability properties of the thermoset. Typically, chemical modification of a clay involves replacing sodium ions with ammonium to form quaternary ammonium salts.

Specific curing agents include, but are not limited to, bis(4-(4-aminophenoxy)phenylsulfone (p-BAPS), bis(4-(3-aminophenoxy)phenylsulfone (m-BAPS), 1,4-bis(3-aminophenoxy)benzene (p-APB), 1,12-diaminododecane, diphenylamine, epoxy amine hardener, 1,6-hexanediamine, 1,3-phenylenediamine, 1,4-phenylenediamine, p-toluene sulfonic acid, cuprous iodide, cuprous bromide, 1,3-bis(3-aminophenoxy)benzene (m-APB), 3,3'-dimethyl-4,4'-diaminodiphenyl sulfone, 3,3'-diethoxy-4,4'-diaminodiphenylsulfone, 3,3'-dicarboxy-4,4'-diaminodiphenylsulfone, 3,3'-dihydroxy-4,4'-diaminodiphenyl sulfone, 3,3'-disulfo-4,4'-diaminodiphenylsulfone, 3,3'-diaminobenzophenone, 4,4'-di aminobenzophenone, 3,3'-dimethyl-4,4'-diaminobenzophenone, 3,3'-dimethoxy-4,4'-diaminobenzophenone, 3,3'-dicarboxy-4,4'-diaminobenzophenone, 3,3'-dihydroxy-4,4'-diaminobenzophenone, 3,3'-disulfo-4,4'-diaminobenzophenone, 4,4'-diaminodiphenyl ethyl phosphine oxide, 4,4'-diaminodiphenyl phenyl phosphine oxide, bis(3-aminophenoxy-4'-phenyl)phenyl phosphine oxide, methylene dianiline, hexakis(4-aminophenoxy)cyclotriphosphazene, 3,3'-dichloro-4,4'-diaminodiphenylsulfone, 2,2'-bis(trifluoromethyl)-4,4'-diaminobiphenyl, 2,2'-bis(4-aminophenyl)hexafluoropropane, bis [4-(4-aminophenoxy)phenyl]2,2'-hexafluoropropane, 1,1-bi s(4-aminophenyl)-1-phenyl-2,2,2-trifluoroethane, 3,3'-dichloro-4,4'-diaminobenzophenone, 3,3'-dibromo-4,4'-diaminobenzophenone, aniline-2-sulfonic acid, 8-aniline-1-naphthalenesulfonic acid, benzene sulfonic acid, butylsulfonic acid, 10-camphorsulfonic acid, 2,5-diaminobenzenesulfonic acid, 6-dimethylamino-4-hydroxy-2-naphthalenesulfonic acid, 5-dimethylamino-1-naphthalene sulfonic acid, 4-hydroxy-3-nitroso-1-naphthalenesulfonic acid tetrahydrate, 8-hydroxyquinoline-5-sulfonic acid, methylsulfonic acid, phenylboric acid, 1-naphthalenesulfonic acid, 2-naphthalenesulfonic acid, 1,5-naphthalenedisulfonic acid, 2,6-naphthalenedisulfonic acid, 2.7-naphthalenedisulfonic acid, picrylsulfonic acid hydrate, 2-pyridineethane sulfonic acid, 4-pyridineethanesulfonic acid, 3-pyridine sulfonic acid, 2-pyridinylhydroxymethanesulfonic acid, sulfanilic acid, 2-sulfobenzoic acid hydrate, 5-sulfosalicylic acid hydrate, 2,4-xylenesulfonic acid, sulfonic acid containing dyes, organic phosphorus-containing acids, phenylphosphinic acid, diphenylphosphinic acid, propylphosphonic acid, 1-aminoethylphosphonic acid, 4-aminophenylphosphonic acid, butylphosphonic acid, t-butylphosphonic acid, 2-carboxyethylphosphonic acid, 2-chloroethylphosphonic acid, dimethylphosphonic acid, ethylphosphonic acid, methylenediphosphonic acid, methylphosphonic acid, phosphonoacetic acid, bis(hydroxymethyl) phosphonic acid, chloromethylphosphonic acid, di-n-butylphosphonic acid, dichloromethylphosphonic acid, diphenyldithiophosphonic acid, 1,2-ethylenediphosphonic acid, n-hystaderylphosphonic acid, hydroxymethylphosphonic acid, n-octadecylphosphonic acid, n-octylphosphonic acid, phenylphosphonic acid, propylenediphosphonic acid, n-tetradecylphosphonic acid, concentrated sulfuric acid, phenylphosphonic acid, copper, iron, zinc, nickel, chromium, molybdenum, vanadium, beryllium, silver, mercury, tin, lead, antimony, calcium, barium, manganese, magnesium, cobalt, palladium, platinum, cuprous bromide, cuprous cyanide, cuprous ferricyanide, zinc chloride, zinc bromide, zinc iodide, zinc cyanide, zinc ferrocyanide, zinc acetate, zinc sulfide, silver chloride, ferrous chloride ferric chloride, ferrous ferricyanide, ferrous chloroplatinate, ferrous fluoride, ferrous sulfate, cobaltous chloride, cobaltic sulfate, cobaltous cyanide, nickel chloride, nickel cyanide, nickel sulfate, nickel carbonate, stannic chloride, stannous chloride hydrate, stannous chloride dihydrate, aluminum nitrate hydrate, aluminum nitrate nonahydrate, triphenylphosphine oxide complex, montmorillonite, chemically modified montmorillonite, 4,4'-(1,3-phenylenedioxy)dianiline, 4,4'-(1,4-phenylenedioxy)dianiline, bis(4-(4-aminophenoxy)phenyl]sulfone, 4,4'-(4,4'-isopropylidenediphenyl-1,1'-diyldioxy)dianiline, 4,4'-(1,3-phenylenediisopropylidene)dianiline, 4,4'-(1,4-phenylenediisopropylidene)dianiline, 4,4'-(1,1'-biphenyl-4,4'-diyldioxy)dianiline, 4,4'-methylenedianiline, 4,4'-sulphonyldianiline, 4,4'-methylene-bis(2-methylaniline), 3,3'-methylenedianiline, 3,4'-methylenedianiline, 4,4'-oxydianiline, 4,4'-(isopropylidene)dianiline, 4,4'-(hexafluoroisopropylidene)dianiline, 4,4'-(hexafluoroisopropylidene)bis (p-phenyleneoxy)dianiline, 4,4'-diaminobenzophenone, the compounds

4,4'-(1,4-phenylenebis(oxy))bis(3-(trifluoromethyl)aniline)
Chemical Formula: $C_{20}H_{14}F_6N_2O_2$
Molecular Weight: 428.33

4,4'-(((perflouoropropane-2,2-diyl)bis(4,1-phenylene))bis(oxy))dianiline
Chemical Formula: $C_{27}H_{20}F_6N_2O_2$
Molecular Weight: 518.46

4,4'-(perflouoropropane-2,2-diyl)dianiline
Chemical Formula: $C_{15}H_{12}F_6N_2$
Molecular Weight: 334.27

2,2'Bis(trifluoromethyl)benzidine
Chemical Formula: $C_{14}H_{10}F_6N_2$
Moledular Weight: 320.24

4,4'-(perflouoropropane-2,2-diyl)diphenol
Chemical Formula: $C_{15}H_{10}F_6N_2$
Molecular Weight: 336.23 and mixtures thereof.

The curing agent may be present in the thermosetting composition in an amount of at least about 0.5% by weight, or at least about 1% by weight, or at least about 2% by weight, or at least about 5% by weight, or at least about 10% by weight, at least about 15% by weight or even at least about 20% by weight, based on the total weight of the thermosetting composition. In other embodiments, the curing agent may be present in an amount of less than about 40% by weight, or less than about 35% by weight, or less than about 30% by weight, or less than about 25% by weight, based on the total weight of the thermosetting composition. In still other embodiments, the curing agent may be present in an amount of between about 0.25% by weight to about 45% by weight, or between about 1% by weight to about 40% by weight, based on the total weight of the thermosetting composition.

The thermosetting composition may also include a second phthalonitrile monomer besides those of the present disclosure, as well as optional additives, to impart desirable structural and/or thermal properties. The additives may include, but not limited to, fillers, for example, carbon nanotubes, clays, carbon nanofibers, metal oxides, zinc oxides, diatomaceous earth, barium sulfate, talc, silica, calcium carbonate, calcium fluoride and combinations thereof, colorants, anti-oxidant stabilizers, thermal degradation stabilizers, light stabilizers, flow agents, bodying agents, flatting agents, binders, blowing agents, fungicides, bactericides, surfactants, plasticizers, rubber tougheners, and other additives known to those skilled in the art. These additives, if present, are added in an amount effective for their intended purpose.

The curing agent (and optionally other phthalonitrile monomers and/or additives) may be added to the functionalized phthalonitrile monomer in any desired order and mixed using customary devices, such as a stirred vessel, stirring rod, ball mill, sample mixer, static mixer or ribbon blended to form the thermosetting composition. The composition may then be cured to form the thermoset polymer. The expression "cured" as used herein, denotes the conversion of the above thermosetting composition into an insoluble and infusible crosslinked product, with simultaneous shaping to give a shaped article such as a molding, pressing or laminate or to give a two-dimensional structure such as a coating, enamel, or adhesive bond. Typical curing processes include ambient temperature cure to elevated temperature cure using thermal, radiation or any combination of energy sources In addition, curing may occur in one or more curing stages. Typical curing temperatures may range from between about 50° C. to about 500° C., such as between about 75° C. to about 375° C. or between about 80° C. to about 300° C. for a time sufficient to at least partially or substantially or fully cure the composition such as, for example, a time ranging from 4 to 20 hours, or from 4 to 16 hours, or 6 to 12 hours.

In still another embodiment, the thermosetting composition may include a second thermoset resin comprising at least one of a vinyl, ethynyl, maleimide, imino, cyano, oxazine or epoxy group. Combining the functionalized phthalonitrile monomer of the present disclosure with such a second thermoset resin will render a thermosetting composition that may exhibit a lower viscosity, a fast curing matrix and after curing, produce a thermoset polymer having a wide range of improved properties such as a higher thermal resistance, improved mechanical performance, lower water absorption, flame retardancy and high char yield.

Thus, according to one particular embodiment, the functionalized phthalonitrile monomer of the present disclosure may be combined with a monofunctional benzoxazine or multifunctional benzoxazine or combination thereof and any one or more of the curing agents and optional additives or a second phthalonitrile monomer besides the functionalized phthalonitrile monomer of the present disclosure as described above to form a thermosetting composition.

According to one embodiment, the monofunctional benzoxazine is an acetylene-bearing benzoxazine compound. Such acetylene-bearing benzoxazine compounds are described in WO 1999/18092, the contents of which are incorporated herein by reference. In particular, the acetylene-bearing benzoxazine compound may be prepared from the reaction of a monophenolic compound, an aldehyde and a primary amine.

The phenol-type compound may be a monophenolic compound, such as, but not limited to, phenol cresol, 2-bromo- 4-methylphenol, 2-allylphenol, 1,4-aminophenol and the like. In one particular embodiment, the phenol-type compound is phenol.

The aldehyde compound may be, but is not limited to, formaldehyde, paraformaldehyde, polyoxymethylene or a compound having the formula $R_aCHO$ where $R_a$ is a $C_1$-$C_{12}$ aliphatic group. In one particular embodiment, the aldehyde compound is formaldehyde.

The primary amine may be an amine having from 2-40 carbons with one or more carbon to carbon triple bond groups and optionally an O, N, S or halogen heteroatom. Intermediate between the nitrogen of the primary amine and the carbon to carbon triple bond group optionally can be a $C_1$-$C_6$ alkyl group optionally substituted with an aromatic group having 6-12 carbons or an aromatic group having 6-12 carbons optionally substituted with a $C_1$-$C_6$ alkyl group. The carbon to carbon triple bond group includes those having the formula —C≡$CR_d$, —$CH_2$—C≡$CR_d$, where $R_d$ is hydrogen, a $C_1$-$C_5$ alkyl group optionally substituted with an aromatic group having 6-12 carbons or an aromatic group having 6-12 carbons optionally substituted with a $C_1$-$C_5$ alkyl group. In one particular embodiment, the primary amine having one or more carbon to carbon triple bonds is 3-aminophenylacetylene.

According to another embodiment, the multifunctional benzoxazine is a compound having the formula wherein b is an integer ranging from 2 to 4; each R is independently hydrogen, a substituted or unsubstituted $C_1$-$C_{20}$ alkyl group, a substituted or unsubstituted $C_2$-$C_{20}$ alkenyl group, a substituted or unsubstituted $C_6$-$C_{20}$ aryl group, a substituted or unsubstituted $C_2$-$C_{20}$ heteroaryl group, a substituted or unsubstituted $C_4$-$C_{20}$ carbocyclic group, a substituted or unsubstituted $C_2$-$C_{20}$ heterocyclic group, or a $C_3$-$C_8$ cycloalkyl group; each $R_1$ is independently hydrogen, a $C_1$-$C_{20}$ alkyl group, a $C_2$-$C_{20}$ alkenyl group, or a $C_6$-$C_{20}$ aryl group; and when b is 2, Z is a direct bond, a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group, O, S, S═O, O═S═O or C═O, and when b is 3 or 4, Z is a substituted or unsubstituted $C_1$-$C_{20}$ alkyl group, a substituted or unsubstituted $C_6$-$C_{20}$ aryl group, a substituted or unsubstituted $C_2$-$C_{20}$ heteroaryl group. Substituents include, but are not limited to, hydroxy, $C_1$-$C_{20}$ alkyl, $C_2$-$C_{10}$ alkoxy, mercapto, $C_3$-$C_8$ cycloalkyl, $C_6$-$C_{14}$ heterocyclic, $C_6$-$C_{14}$ aryl, $C_6$-$C_{14}$ heteroaryl, halogen, cyano, nitro, nitrone, amino, amido, acyl, oxyacyl, carboxyl, carbamate, sulfonyl, sulfonamide and sulfuryl.

According to one embodiment, the multifunctional benzoxazine compound above is a compound obtained from the reaction of a multifunctional phenolic compound, an aldehyde, such as formaldehyde, and a primary amine.

The multifunctional phenolic compound may be, but is not limited to, resorcinol, bisphenol A, bisphenol F, bisphenol E, bisphenol S, 1,2,2,2-tetraphenolethane, thiodiphenol, phenolphthalein, dicyclopentadienyidiphenol, 1,8-hydroxyanthraquinone, 1,6-dihydroxynaphthalene, 2-2'-dihydroxyazobenzene and 1,3,5-trihydroxybenzene.

The primary amine may be, but is not limited to, those primary amines having at least one carbon to carbon triple bond group described above, as well as aniline, o-, m- and p-phenylene diamine, benzidine, 4,4'-diaminodiphenyl methane, cyclohexylamine, 1,4-diaminocyclohydexyl, butylamine, methylamine, hexylamine, allylamine, furfurylamine, ethylenediamine, propylenediamine and diaminodiphenyl sulfone.

According to one embodiment, the thermosetting composition may contain the monofunctional benzoxazine or multifunctional benzoxazine or combination thereof and the functionalized phthalonitrile monomer in weight ratio of total benzoxazine:functionalized phthalonitrile monomer of between about 1:1 to about 10:1, or from about 1.5:1 to about 10:1, or from about 2:1 to about 10:1.

The thermosetting composition may be prepared as described above by mixing in any order at least one monofunctional benzoxazine or multifunctional benzoxazine with the functionalized phthalonitrile monomer and optional curing agent, other phthalonitrile monomers besides the functionalized phthalonitrile monomers of the present disclosure and additives using customary devices, such as a stirred vessel, stirring rod, ball mill, sample mixer, static mixer or ribbon blended to form the thermosetting composition. The thermosetting composition may then be cured as described above to form the thermoset polymer.

In still another embodiment, there is provided a thermoset polymer obtained by contacting any suitable substrate with any one of the thermosetting compositions described above and subjecting the substrate/thermosetting composition to thermal, radiation or a combination of energy sources to cure the substrate/thermosetting composition. In one embodiment, the thermosetting compositions of the present disclosure may be used to bond one or more substrates together by contacting one or more surfaces of like or dissimilar substrates that are to be bonded with the thermosetting composition under conditions sufficient to cure the thermosetting composition.

In an alternative embodiment, by curing the thermosetting compositions of the present disclosure, a composite article may be obtained by techniques well known in the industry, for example, pultrusion, infusion, molding, encapsulating or coating. Thus, the thermosetting composition of the present disclosure may be used in methods for manufacturing composite articles, such as castings, prepregs, bonding sheets, laminates and metal-foil clad laminates.

The properties of the composite articles can be tailored for certain applications by the addition of reinforcement fibers.

Examples of reinforcement fibers include glass, quartz, carbon, alumina, ceramic, metallic, aramid, natural fibers (e.g. flax, jute, sisal, hemp), paper, acrylic and polyethylene fibers and mixtures thereof. The reinforcement fibers may be in any of various modes, for example, as a strand or roving formed by paralleling continuous fibers or discontinuous fibers (short fibers) in one direction, cloth such as woven fabric or mat, braids, unidirectional, bi-directional, random, pseudo-isotropic or three-dimensionally dispersed mat-like material, heterogeneous lattice or mesh material, and three-dimensional material such as triaxially woven fabric.

Thus, in another embodiment, there is provided a process for producing a composite article including the steps of: contacting a layer of reinforcement fibers with the thermosetting composition to coat and/or impregnate the reinforcement fibers; and curing the coated and/or impregnated reinforcement fibers to produce the composite article.

Coating and/or impregnation may be affected by either a wet method or hot melt method. In the wet method, the thermosetting composition is first dissolved in a solvent to lower viscosity, after which coating and/or impregnation of the reinforcement fibers is effected and the solvent evaporated off using an oven or the like.

In the hot melt method, coating and/or impregnation may be effected by directly coating and/or impregnating the reinforcement fibers with the thermosetting composition, which may have been heated to reduce its viscosity, or alternatively, a coated film of the thermosetting composition may first be produced on release paper or the like, and the film placed on one or both sides of the reinforcement fibers and heat and pressure applied to effect coating and/or impregnation.

According to another aspect, there is provided a process for producing a composite article in a RTM system. The process includes the steps of: a) introducing a fiber preform comprising reinforcement fibers into a mold; b) injecting the thermosetting composition into the mold, c) allowing the thermosetting composition to impregnate the fiber preform; and d) heating the resin impregnated preform for a period of time to produce an at least partially cured solid article; and optionally e) subjecting the partially cured solid article to additional heat.

In still another embodiment, there is provided a process for forming a composite article in a VaRTM system. The process includes the steps of a) introducing a fiber preform comprising reinforcement fibers into a mold; b) injecting the thermosetting composition into the mold; c) reducing the pressure within the mold; d) maintaining the mold at about the reduced pressure; e) allowing the thermosetting composition to impregnate the fiber preform; f) heating the resin impregnated preform to produce an at least partially cured solid article; and optionally g) subjecting the at least partially cured solid article to additional heat.

Besides RTM and VaRTM systems, the thermosetting composition may be used in other methods and systems for producing composite articles including hot-pressing of prepregs, sheet molding compound, molding, casting, pultrusion and filament winding.

In another embodiment, the thermosetting composition, upon curing, provides a thermoset polymer with excellent well-balanced physical, mechanical and thermal properties. The properties of the thermoset polymer that are well-balanced in accordance with the present disclosure may include at least two of: a glass transition temperature ($T_g$) of greater than about 250° C., or greater than about 270° C., or greater than about 290° C.; a storage modulus greater than 3500 MPa, or greater than 3750 MPa, or greater than 4000 MPa; a viscosity at 75° C. of less than 250 centipoise, or less than 200 centipoise, or less than 175 centipoise; and, a char yield of at least 60%, or at least 65%, or at least 70%.

The thermosetting composition and composite articles of the present disclosure may be used in various applications, for example, in aerospace applications, where they may be employed as aircraft primary structural materials (main wings, tail wing, floor beam, etc.), secondary structural materials (flap, aileron, cowl, fairing, interior trim, etc.), rocket motor cases, structural materials for artificial satellites or other moving bodies such as cars, boats and railway carriages, in drive shafts, fuel cells, plate springs, wind turbine blades, pressure vessels, fly-wheels, papermaking rollers and civil engineering and building materials (roofing materials, cables, reinforcing bars, retrofitting materials).

EXAMPLES

Example 1. Synthesis of Tetramethylbisphenol Furan

Furfuraldehyde        2,6-Xylenol Tetramethyl Bisphenol Furan TMBPF
4,4-(furan-2-ylmethylene)bis(2,6-dimethylphenol)

To a 500 ml 4-neck round bottom flask equipped with a mechanical stirrer and a reflux condenser was charged 61.08 grams of 2,6-xylenol and 32.04 grams of methanol. 2 grams of sodium hydroxide were then added and dissolved with stirring. The resulting mixture was heated to reflux and 24.0 grams of furfural was added dropwise under reflux over a 2 hour time period. The mixture was then refluxed for an additional 15 hours and monitored by HPLC for complete conversion after which the mixture was neutralized with 35 grams of 20% aqueous sodium dihydrogenphosphate. Precipitated crystals were collected by filtration, washed with a 1:1 methanol/water solution and dried in a vacuum drying oven. 72.6 grams of tetramethyl bisphenol furan (90.8%) were produced. The product was found to be very pure on HPLC (99.7%).

Example 2. Synthesis of Tetramethylbisphenol Furan Phthalonitrile 4,4'-(furan-2-ylmethylene)
bis(2,6-dimethylphenol)
Chemical Formula: C$_{21}$H$_{22}$O$_3$
Molecular Weight: 322.40

4,4'-(furan-2-ylmethylene)
bis(2,6-dimethyl-4,1-phenylene))
bis(oxy))diphthalonitrile
Chemical Formula: C$_{37}$H$_{26}$N$_4$O$_3$
Molecular Weight: 574.64

Figure 1:
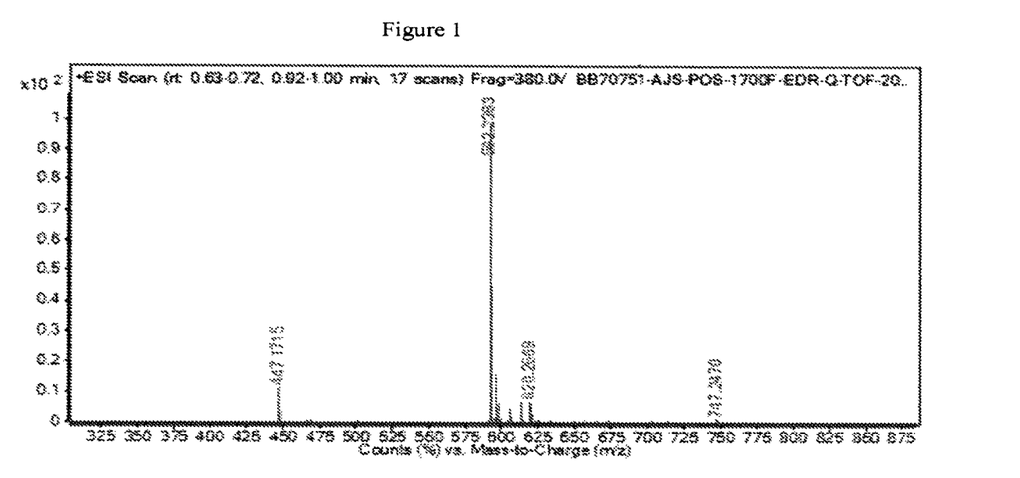
FIG. 1 is an LC-MS chromatogram of the compound produced in Example 2.
Figure 2:
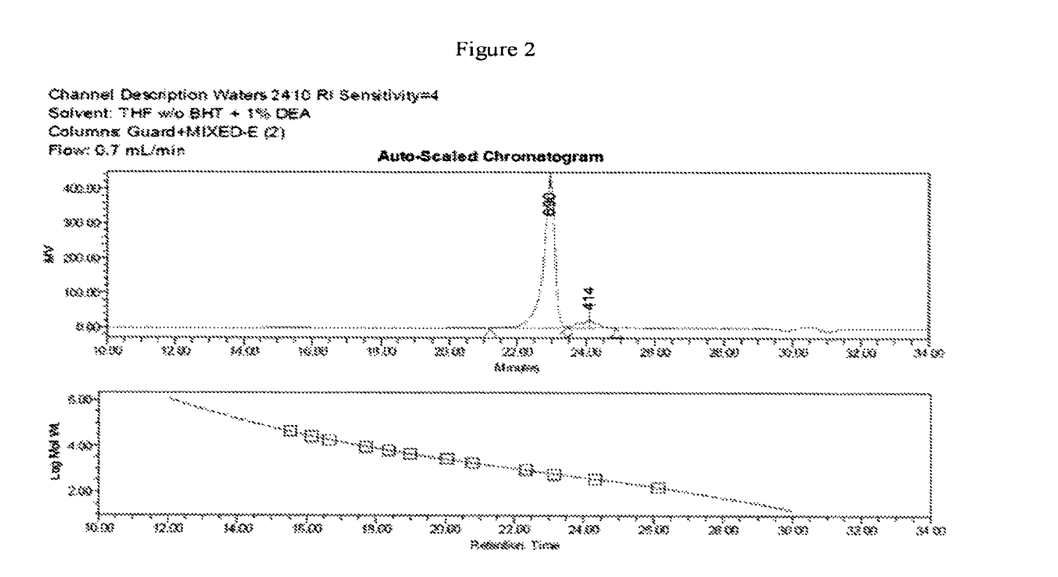
FIG. 2 is a GPC scan of the compound produced in Example 2.
Figure 3:
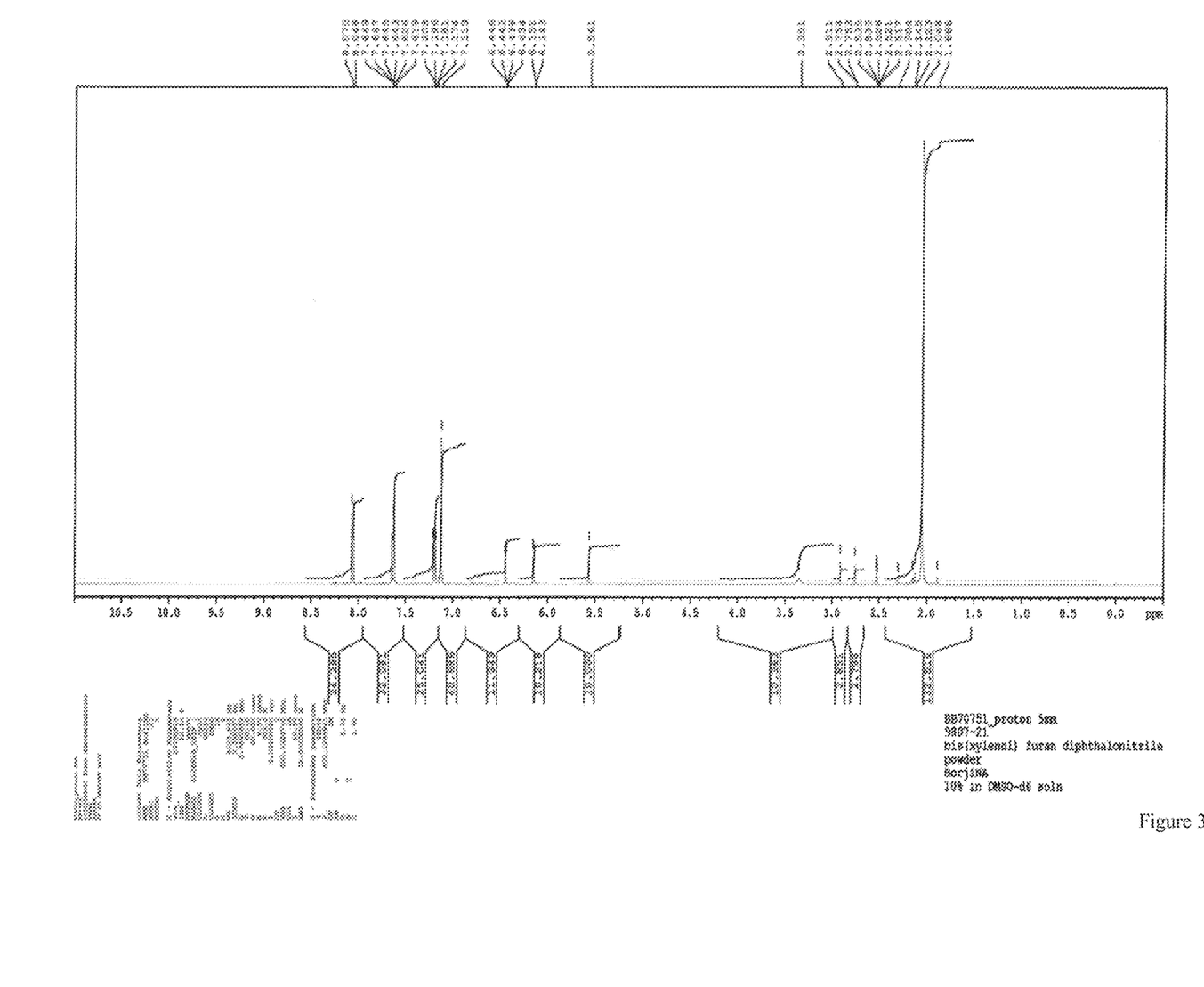
FIG. 3 is a proton NMR of the compound produced in Example 2.
Figure 4:
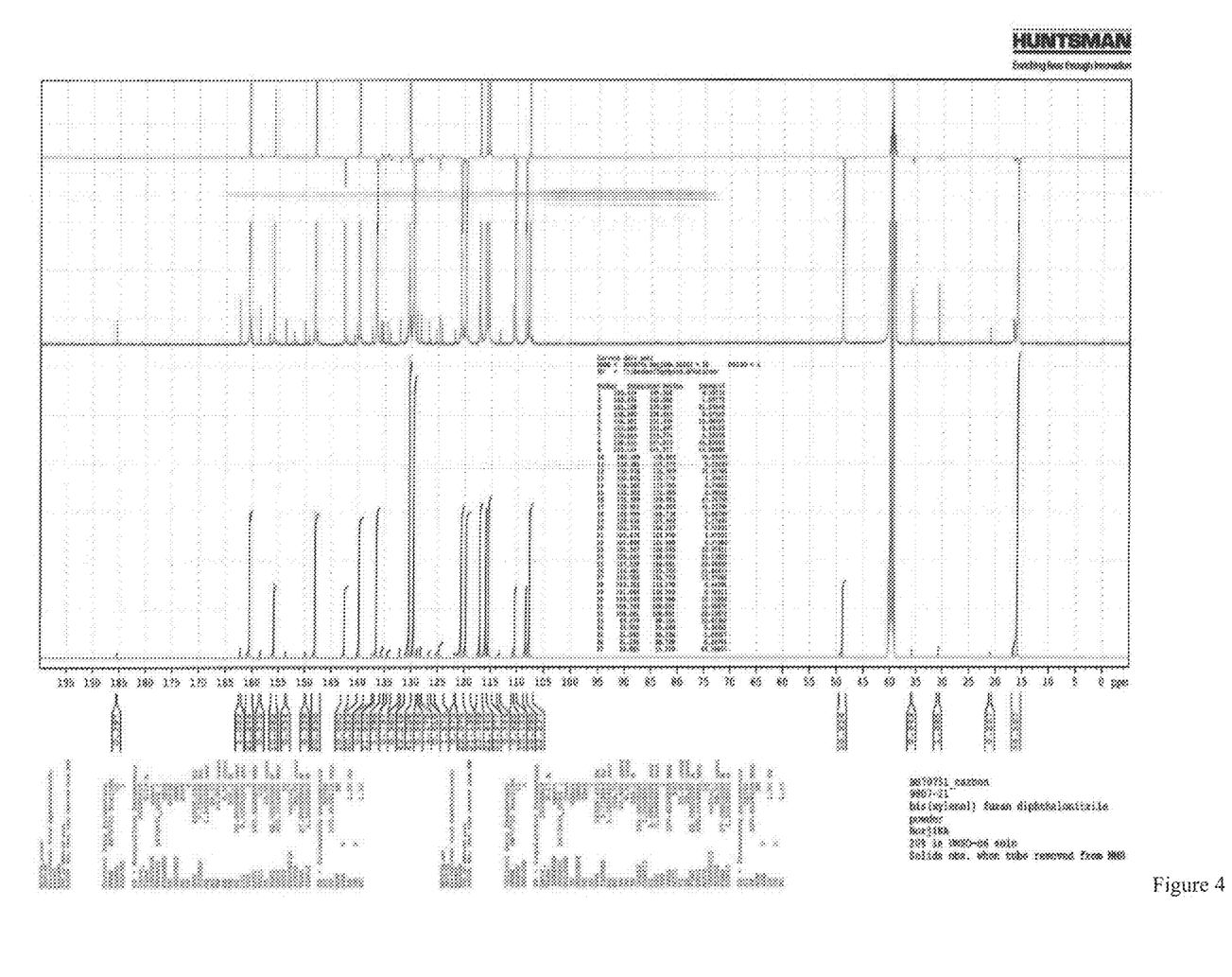
FIG. 4 is a $^{13}$C-NMR of the compound produced in Example 2.
Figure 5:
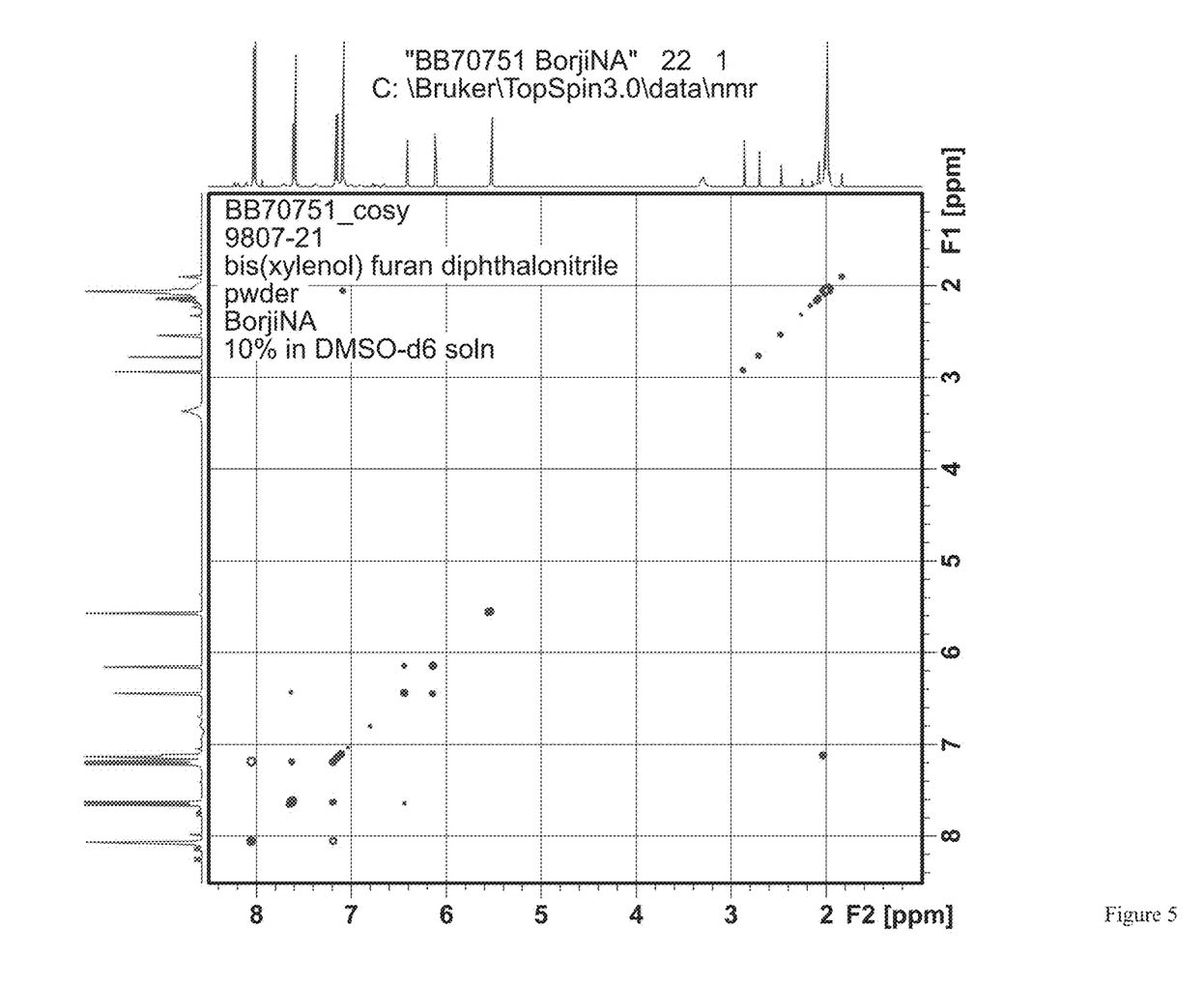
FIG. 5 is a 2-dimensional NMR of the proton-proton COSY spectra of the compound produced in Example 2.
Figure 6:
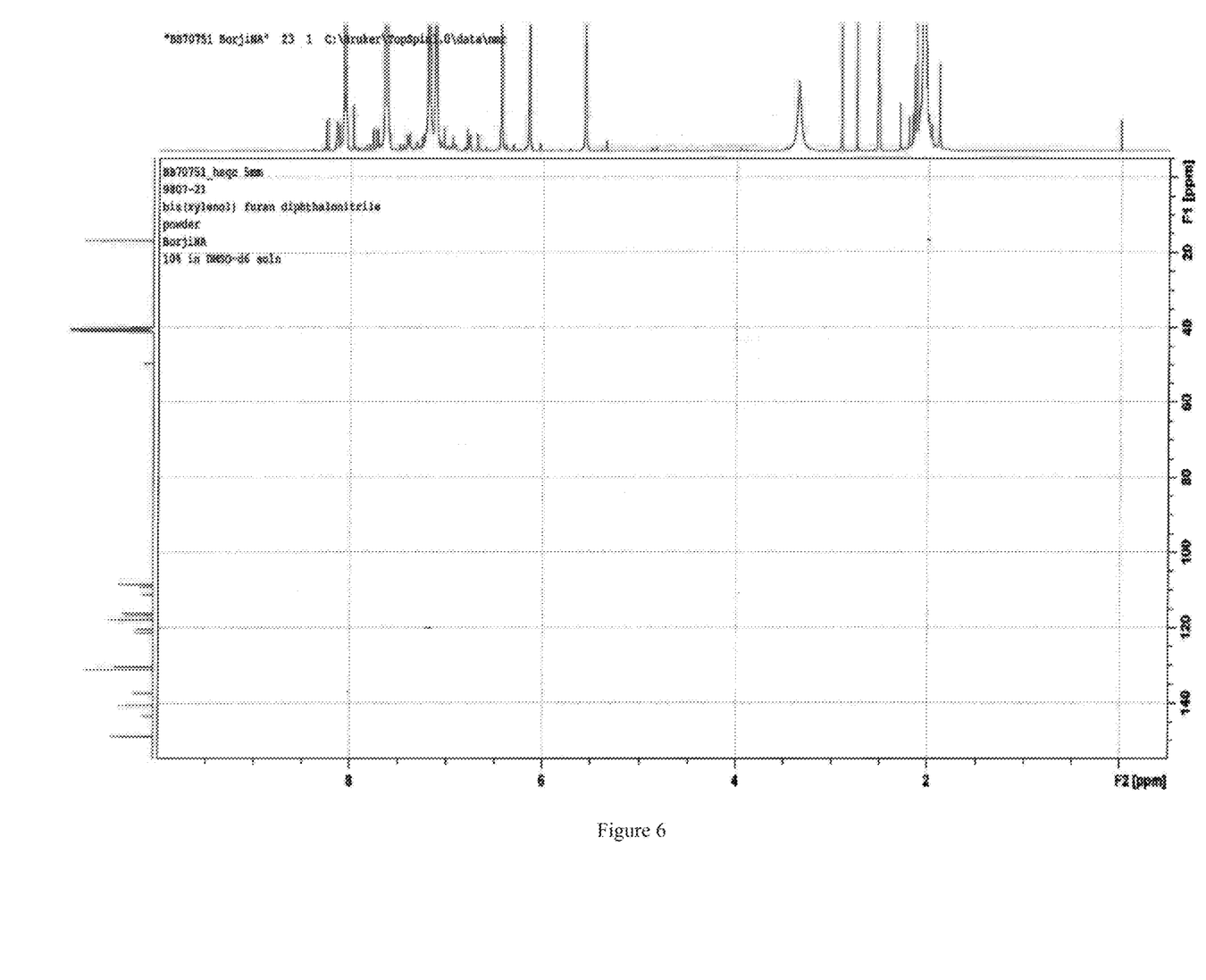
FIG. 6 is a 2-dimensional NMR HSQC spectra of the compound produced in Example 2.
Figure 7:
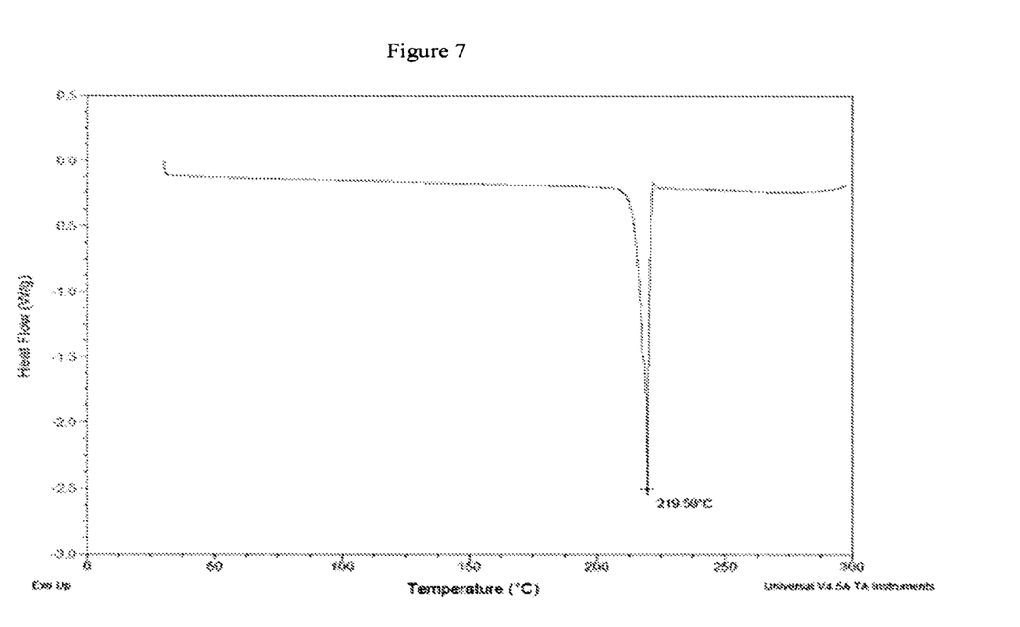
FIG. 7 is the melting point determined by DSC of the compound produced in Example 2.
Figure 8:
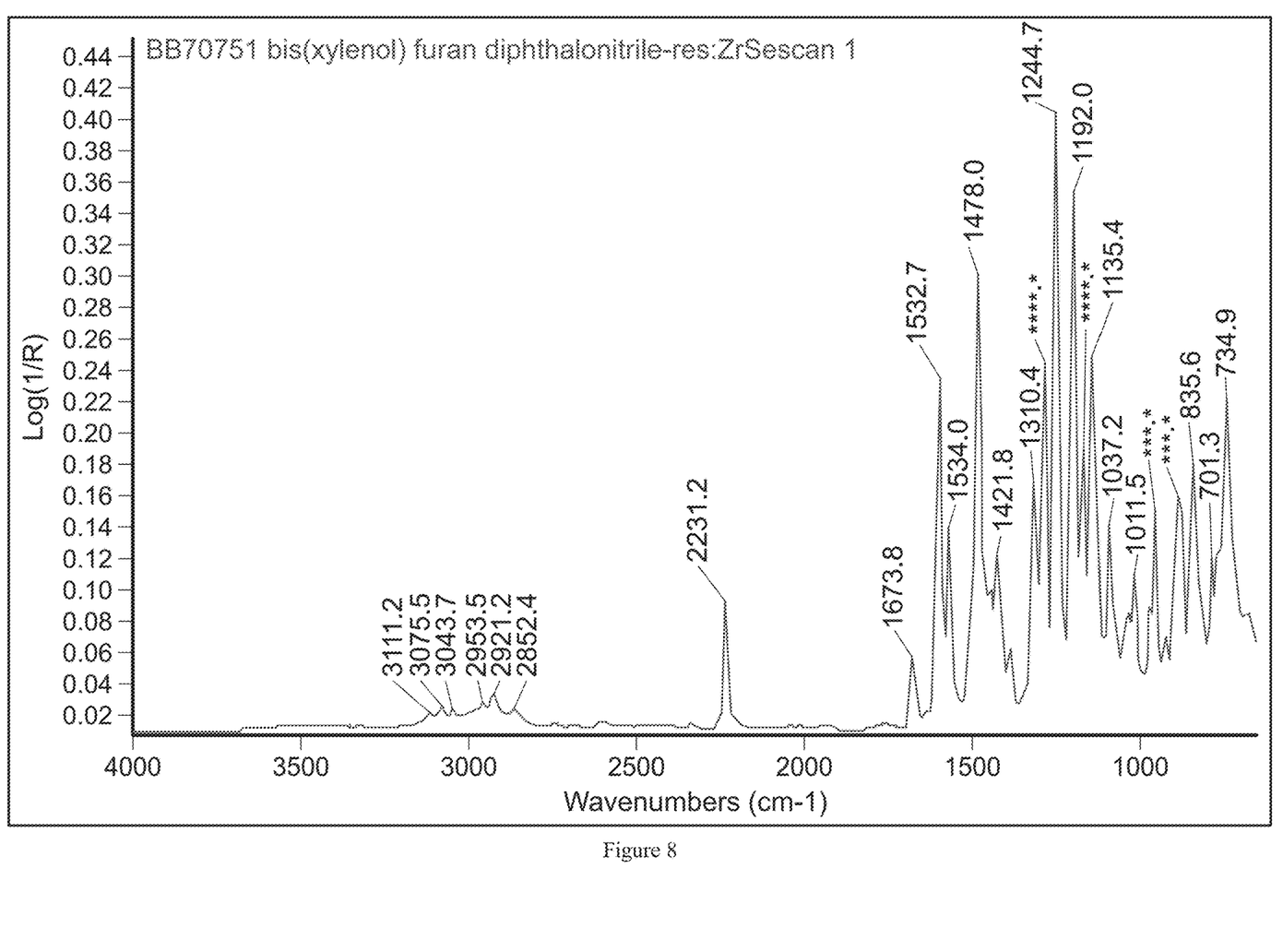
FIG. 8 is an FT-IR spectrum of the compound produced in Example 2.

To a 1000 mL 4-necked round bottom flask fitted with a thermometer, a Dean-Stark trap with condenser, and a nitrogen inlet, were added tetramethyl bisphenol furan from Example 1 (32.2 grams, 0.1 mole), powdered K$_2$CO$_3$ (33.2 grams, 0.24 mole), toluene (100 mL), and N,N-dimethylformamide (DMF) (146.1 grams). The resulting mixture was degassed with nitrogen, and the mixture was heated to reflux at 140° C. for 10-12 hours. The toluene was then removed by distillation and the reaction mixture was cooled to 30° C. 4-nitrophthalonitrile (35.3 grams, 0.204 mole) was then added in one portion and the reaction mixture was heated at 80° C. and monitored by HPLC for complete conversion. The mixture was then cooled to ambient temperature and poured into cold deionized water resulting in the formation of a solid. Precipitated crystals were collected by filtration, washed with cold deionized water until neutral and then washed with 1:1 methanol/water solution. The dark yellow solid that was obtained was vacuum dried to yield 54.5 grams, (95%) of functionalized phthalonitrile monomer product. The structure of this product was confirmed by analysis with LC-MS, GPC, NMR and FTIR. The LC-MS chromatogram of FIG. 1, GPC scan of FIG. 2, NMR's of FIGS. 3-6 and FT-IR spectrum of FIG. 9 are consistent for the targeted tetramethylbisphenol furan phthalonitrile product. The melting point for the tetramethylbisphenol furan phthalonitrile was found to be 219.6° C. as shown in FIG. 8.

Example 3. Functionalized Phthalonitrile Monomer/Benzoxazine

To a 4 oz. glass jar was charged 20 grams of phenol 3-aminophenyl acetylene benzoxazine). The glass jar was then put into an 80° C. oven until the material had melted, and then, while stirring, 6 grams of phthalonitrile (4,4'-(((furan-2-ylmethylene)bis(2,6-dimethyl-4,1-phenylene))bis(oxy))diphthalonitrile) were added to the glass jar. The resulting mixture was stirred occasionally until the added material had dissolved in the melted benzoxazine. About 14 grams of the mixture was then transferred into an aluminum pan. After degassing at 65° C., the mixture was staged cured at 120° C. for 2 hours, 150° C. for 2 hours, 180° C. for 2 hours, and 200° C. for 2 hours. The DSC of the freshly made sample, and the DMA, TGA of one half of the cured product were determined. The other half of the cured product was further post cured at 250° C. for 3 hours and the DMA and TGA of this cured product were determined. The results are shown below in Table 1.

Example 4. Functionalized Phthalonitrile Monomer/Benzoxazine

To a 4 oz. of glass jar, was charged with 12 grams of phenol 3-aminophenyl acetylene benzoxazine). The glass jar was then put into an 80° C. oven until the material had melted, and then, while stirring, 2.4 grams of phthalonitrile (4,4'-(((furan-2-ylmethylene)bis(2,6-dimethyl-4,1-phenylene))bis(oxy))diphthalonitrile) were added to the glass jar. The resulting mixture was stirred occasionally until the added material had dissolved in the melted benzoxazine. About 12.5 grams of the mixture was transferred into an aluminium pan. After degassing at 65° C., the mixture was staged cured at 120° C. for 2 hours, 150° C. 2 hours, 180° C. 2 hours, and 200° C. for 2 hours. The DSC of the fresh made sample, and the DMA, TGA of one half of the cured product were determined. The other half of the cured product was further post cured at 250° C. for 3 hours and the DMA and TGA of this cured product were also determined. The results are shown below in Table 1.

Example 5. Functionalized Phthalonitrile Monomer/Benzoxazine

To a 4 oz. of glass jar, was charged with 10.8 grams of phenol 3-aminophenyl acetylene benzoxazine). The glass jar was then put into an 80° C. oven until the material had melted, and then, while stirring, 5.38 grams of the phthalonitrile (4,4'-(((furan-2-ylmethylene)bis(2,6-dimethyl-4,1-phenylene))bis(oxy))diphthalonitrile) were added to the glass jar. The resulting mixture was stirred occasionally until the added material had dissolved in the melted benzoxazine. About 12.5 grams of the mixture was transferred into an aluminium pan. After degassing at 65° C., the mixture was staged cured at 120° C. for 2 hours, 150° C. 2 hours, 180° C. 2 hours, and 200° C. for 2 hours. The DSC of the freshly made sample, and the DMA, TGA of one half of the cured product were determined. The other half of the cured product was further post cured at 250° C. for 3 hours and the DMA and TGA of this cured product were also determined. The results are shown below in Table 1.

Example 6. Comparative Example

To an aluminum pan was charged with 14 grams of a slightly polymerized phenol 3-aminophenyl acetylene benzoxazine. The aluminum pan was then put into an 80° C. vacuum oven to be melted and degassed for 1 hour. After degassing, the material was staged cured at 120° C. for 2 hours, 150° C. for 2 hours, 180° C. for 2 hours, and 200° C. for 2 hours. The DSC of the fresh made sample, and the DMA, TGA of one half of the cured product were determined. The other half of the cured product was further post cured at 250° C. for 3 hours and the DMA and TGA of this cured product were also determined. The results are shown below in Table 1.

TABLE 1

|  | Ex. 3 | Ex. 4 | Ex. 5 | Comp. Ex. 6 |
|---|---|---|---|---|
| Benzoxazine (grams) | 10 | 10 | 10 | 10 |
| Bisphthalonitrile (grams) | 3 | 2 | 5 | — |
| Viscosity (75°; Pa s) | <0.744 | 0.151 | 0.986 | <0.06 |
| $T_{initial}$ (° C.) | 229.8 | 227.3 | 224.8 | 233.1 |
| $T_{peak}$ (° C.) | 243.0 | 240.1 | 239.7 | 244.6 |
| Delta H (J/g) | 707.1 | 753.8 | 596.4 | 797.9 |
| TGA Char Yield (800° C.) | 70% | 66% | 71% | 54% |
| DMA storage modulus (MPa) | 4249 | 4002 | 3608 | — |
| DMA $T_g$ Onset (° C.) | 215 | 237 | 201 | — |
| DMA $T_g$ Peak (° C.) | 249 | 269 | 234 | — |
| After post cure at 250° C.: |  |  |  |  |
| TGA Char Yield (800° C.) | 69% | — | 72% | 55% |
| DMA storage modulus (MPa) | 4191 | 3925 | 4438 | 4149 |
| DMA $T_g$ Onset (° C.) | 291 | 293 | 262 | 330 |
| DMA $T_g$ Peak (° C.) | 311 | 316 | 314 | 336 |

Although making and using various embodiments of the present invention have been described in detail above, it should be appreciated that the present invention provides many applicable inventive concepts that can be embodied in a wide variety of specific contexts. The specific embodiments discussed herein are merely illustrative of specific ways to make and use the invention, and do not delimit the scope of the invention.

What is claimed is:

1. A functionalized phthalonitrile monomer obtained from the reaction of (i) a polyhydric phenol compound comprising at least one furan group or thiophene group, and (ii) 4-nitrophthalonitrile, wherein the polyhydric phenol compound comprising at least one furan group or thiophene group is a compound selected from the formulas (2) to (7) and (9) to (10)

(2)

(3)

(4)

(5)

(6)

(7)

(9)

(10)

where n is an integer from about 3 to about 3.2.

* * * * *